United States Patent
Bressner et al.

(10) Patent No.: US 12,310,854 B2
(45) Date of Patent: May 27, 2025

(54) ORTHOPAEDIC IMPLANT TO ADMINISTER A MEDICAL SUBSTANCE

(71) Applicant: The Johns Hopkins University, Baltimore, MD (US)

(72) Inventors: Jarred A. Bressner, Baltimore, MD (US); Mikhail Osanov, Baltimore, MD (US); Adam Levin, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 324 days.

(21) Appl. No.: 17/597,215

(22) PCT Filed: Jul. 22, 2020

(86) PCT No.: PCT/US2020/043090
§ 371 (c)(1),
(2) Date: Dec. 29, 2021

(87) PCT Pub. No.: WO2021/021521
PCT Pub. Date: Feb. 4, 2021

(65) Prior Publication Data
US 2022/0241076 A1 Aug. 4, 2022

Related U.S. Application Data

(60) Provisional application No. 62/881,247, filed on Jul. 31, 2019.

(51) Int. Cl.
*A61F 2/38* (2006.01)
*A61F 2/28* (2006.01)
(Continued)

(52) U.S. Cl.
CPC .................. *A61F 2/30* (2013.01); *A61F 2/28* (2013.01); *A61F 2/4455* (2013.01);
(Continued)

(58) Field of Classification Search
CPC .. A61F 2/30; A61F 2/28; A61F 2/4455; A61F 2002/30593; A61F 2002/30677;
(Continued)

(56) References Cited

U.S. PATENT DOCUMENTS 8,500,819 B2 * 8/2013 Meridew ........... A61M 5/14276
604/48
9,445,901 B2 * 9/2016 Tunc ................... A61F 2/30767
(Continued)

OTHER PUBLICATIONS

International Search Report and Written Opinion issued in International Application No. PCT/US2020/043090; Dated Oct. 29, 2020.

*Primary Examiner* — Ann Hu
(74) *Attorney, Agent, or Firm* — Harrity & Harrity, LLP

(57) ABSTRACT

An orthopaedic implant with a medical dosing capability is disclosed herein. The orthopaedic implant may include a structure configured to interact with a bone of the patient. The orthopaedic implant may include a reservoir associated with the structure to hold a medical substance for treating a health condition of the patient. The orthopaedic implant may include a dosing mechanism to release the medical substance to treat the health condition.

20 Claims, 7 Drawing Sheets

(51) Int. Cl.
*A61F 2/30* (2006.01)
*A61F 2/40* (2006.01)
*A61F 2/44* (2006.01)

(52) U.S. Cl.
CPC ............... *A61F 2002/30593* (2013.01); *A61F 2002/30677* (2013.01); *A61F 2002/3068* (2013.01); *A61F 2002/3092* (2013.01); *A61F 2002/3093* (2013.01)

(58) Field of Classification Search
CPC ...... A61F 2002/3068; A61F 2002/3092; A61F 2002/3093
See application file for complete search history.

(56) References Cited

U.S. PATENT DOCUMENTS

| | | | |
|---|---|---|---|
| 9,561,354 B2* | 2/2017 | Nebosky | A61B 17/866 |
| 10,022,233 B1* | 7/2018 | Gall | A61L 27/56 |
| 2006/0057737 A1* | 3/2006 | Santini, Jr. | A61K 9/0009 |
| | | | 604/890.1 |
| 2007/0016163 A1* | 1/2007 | Santini, Jr. | A61L 27/56 |
| | | | 604/890.1 |
| 2009/0163965 A1* | 6/2009 | Boyden | A61L 2/0011 |
| | | | 607/3 |
| 2010/0042218 A1* | 2/2010 | Nebosky | A61F 2/3094 |
| | | | 623/17.11 |
| 2010/0130959 A1* | 5/2010 | Boyd | A61B 17/80 |
| | | | 604/93.01 |
| 2010/0211120 A1* | 8/2010 | Bonutti | A61B 17/8685 |
| | | | 606/86 R |
| 2010/0217401 A1* | 8/2010 | de Beaubien | A61F 2/38 |
| | | | 623/20.36 |
| 2010/0222750 A1* | 9/2010 | Cheng | A61F 2/442 |
| | | | 606/246 |
| 2011/0022174 A1* | 1/2011 | Holdstein | G06T 17/20 |
| | | | 382/128 |
| 2012/0029638 A1* | 2/2012 | Miller | A61F 2/44 |
| | | | 623/17.11 |
| 2012/0109304 A1* | 5/2012 | Balckwell | A61N 5/1014 |
| | | | 623/17.12 |
| 2015/0230874 A1 | 8/2015 | Musuvathy et al. | |
| 2016/0339152 A1* | 11/2016 | Bonutti | A61L 27/56 |
| 2017/0028127 A1* | 2/2017 | U.R.Anoop | A61K 31/137 |
| 2018/0021554 A1* | 1/2018 | Nebosky | A61B 17/80 |
| | | | 604/288.04 |

* cited by examiner

ORTHOPAEDIC IMPLANT TO ADMINISTER A MEDICAL SUBSTANCE

CROSS-REFERENCE TO RELATED APPLICATIONS

This Patent Application is a 371 national stage of PCT Application PCT/US2020/043090 filed on Jul. 22, 2020, entitled "ORTHOPAEDIC IMPLANT TO ADMINISTER A MEDICAL SUBSTANCE," which claims priority to U.S. Provisional Patent Application No. 62/881,247, filed on Jul. 31, 2019, and entitled "ORTHOPAEDIC IMPLANT TO ADMINISTER A MEDICAL SUBSTANCE," both of which are hereby expressly incorporated by reference herein.

BACKGROUND

Orthopaedic implants provide support and/or rehabilitation to a bone and/or skeletal structure of a patient. For example, a bone implant may be fused with a bone to ensure that the bone heals properly, grows properly, and/or the like. An arthroplasty implant may be a bone implant that is fused with a bone that is associated with a joint of a patient (e.g., a shoulder, a knee, a hip, and/or the like), to rehabilitate and/or replace a portion of the joint. An interbody orthopaedic implant, such as an interbody spine implant, may be configured to provide support between one or more bones (e.g., vertebra) of a patient.

SUMMARY

According to some implementations, an orthopaedic implant for treating a patient may include a structure configured to interact with a bone of the patient; a reservoir associated with the structure to hold a medical substance for treating a health condition of the patient; and a dosing mechanism to release the medical substance to treat the health condition.

According to some implementations, a medical substance dosing system may include an orthopaedic implant comprising a structure configured to interact with a bone of a patient and a dosing mechanism to release a medical substance to treat a health condition of the patient; and a supply mechanism configured to supply the dosing mechanism with the medical substance.

According to some implementations, a method for providing a medical substance to treat a patient may include configuring an orthopaedic implant to release the medical substance; supplying a dosing mechanism, of the orthopaedic implant, with the medical substance; and implanting the orthopaedic implant to interact with a bone of a patient to cause the orthopaedic implant to release the medical substance.

DETAILED DESCRIPTION

Figure 1:
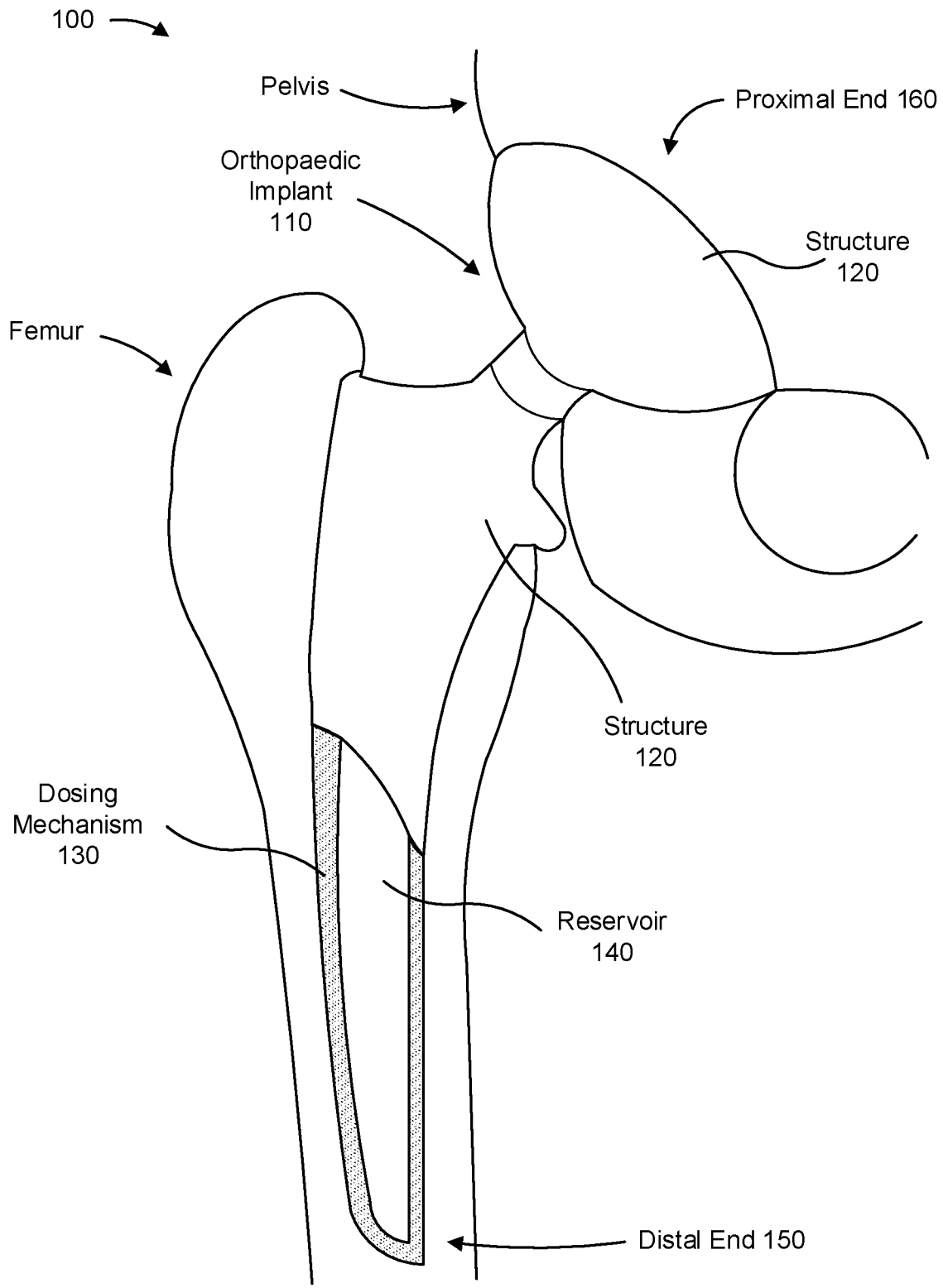
FIG. 1 is a diagram of an example implementation of an orthopaedic implant described herein.

The following detailed description of example implementations refers to the accompanying drawings. The same reference numbers in different drawings may identify the same or similar elements.

In some instances, after a patient is implanted with an orthopaedic implant through a surgical procedure, the orthopaedic implant may be associated with an infection, with pain, with bone healing, with bone ingrowth, with bone ongrowth, and/or the like. Furthermore, concerns regarding the above may develop after the orthopaedic implant has been surgically placed, or the surgical procedure may be performed with the goal of combating the above items of concern at the time of an index operation. As examples, such a surgical procedure (which may be a primary or revision procedure) and/or orthopaedic implant may be associated with a total hip arthroplasty, a total knee arthroplasty, a total ankle arthroplasty, a total shoulder arthroplasty, a total elbow arthroplasty, mega-prostheses, trauma intramedullary rods, spinal fusion implants (posterior spinal fusion or anterior spinal fusion), and/or the like. In such cases, patients may be treated with a plurality of medications (e.g., pain medications, antimicrobial agents (e.g., antibiotic agents, antifungal agents, a deoxyribonuclease (DNase), and/or the like), stimulants (e.g., bone growth promoting agents, such as bone morphogenic proteins, and/or the like), inhibitors (e.g. antiresorptive agents, such as bisphosphonates, RANK-L inhibitors, and/or the like), anesthetics, and/or the like). Typically, the patient is administered with such medications, orally, intravenously, and/or subcutaneously.

More specifically, with respect to orthopaedic infections (which can result in expensive, devastating, morbid, and catastrophic experiences for the patient), one or more additional surgical procedures may be required (e.g., to eradicate biofilm production). In some instances, one or more of the surgical procedures may involve placement of a peripherally inserted central catheter (PICC) line for a relatively long duration (e.g., a minimum of 4-6 weeks) to administer intravenous (IV) antibiotics. The presence of a PICC line, itself, poses risk of bloodstream infections and sepsis such that bloodstream infections can have life threatening consequences. Additionally, since a tip of an internal portion of the PICC line terminates in a cavoatrial junction of the patient's heart, there is a risk of line migration which can trigger cardiac arrhythmias and/or other effects. Furthermore, the PICC line can be uncomfortable and unsightly to the patient, can interfere with activities of daily living, and can require the patient to remain attached to an IV line at home and/or in an infusion clinic for administration of the antibiotics several times per day (e.g., the dosing interval may be dependent on the antibiotic agent). An antibiotic infused through the PICC line is administered systemically in hopes that a portion of the administered dose is delivered to the site of the infection and that the portion satisfies the minimum inhibitory concentration or minimum killing concentration where the antibiotic is needed to allow clearance of the infection. Moreover, administration of high doses of these antibiotic agents themselves have side effects (e.g., risk of nephrotoxicity (kidney damage), ototoxicity (hearing loss), and/or the like). Accordingly, there can be a relatively thin margin of error when it comes to determining a dose that is high enough to ensure that a satisfactory portion is administered, systemically, to the area of infection without causing other harmful side effects.

In some instances, for infections following a total joint orthopaedic implantation, a subsequent surgery may be performed to remove the infected implant with simultaneous debridement of surrounding tissue. At the time of the surgery, an antibiotic spacer is often placed with a mass of bone cement mixed with an antibiotic powder. Often, the antibiotic spacer is a non-articulating spacer, and, therefore, a patient administered with such an antibiotic spacer would be unable to bend a limb associated with the joint. Furthermore, following placement of such antibiotic spacers (which have been shown to be ineffective in clearing the infection, may elute antibiotics within a relatively short-time period, and may be placed along with a PICC line), the patient needs to be frequently monitored (e.g., through images from a medical imaging device), and finally undergo an additional surgery for placement of a revised functional total joint orthopaedic implant, which is very technically challenging and morbid due to large amounts of bone lost through the process of treating the infection and reactive changes of the surrounding tissues.

With respect to pain management following placement of an orthopaedic implant, post-operative pain is typically managed with pain medications, including opioids, which can have known life-threatening complications if administered incorrectly, and have known risks of dependence and addiction potential. In some instances, local pain medications (e.g., non-opioids) are locally injected into the tissues around the surgical site in an attempt to reduce post-operative pain (and/or opioid use). However, the effective duration of these injections is variable (e.g., relative to characteristics of the patient, results of the surgery, and/or the like) and relatively short acting. Additionally, or alternatively, a nerve block can be administered (which can involve similar challenges of having a variable and relatively short effective duration) but can involve a risk of nerve injury during placement of an injection needle around the nerve to administer the block.

Typically, an orthopaedic implant placement includes a goal of promoting bone growth on and into the implant and/or toward union of a fractured bone or fusion segment. Certain medications are known to hasten this process, but, under previous techniques, administration of such medications comes with the same or similar complications as administering an antibiotic (e.g., ensuring a sustained low-dose tissue concentration).

According to some implementations described herein, an orthopaedic implant is configured to administer medical substances to a patient following placement of the orthopaedic implant. The orthopaedic implant may include a dosing mechanism that is configured to release the medical substance to the surgical area via a dosing mechanism of the orthopaedic implant. Accordingly, the orthopaedic implant may permit the medical substance to be released directly to the surgical area precisely where its desired medical action is targeted rather than indirectly (or systemically) through a digestive system, cardiovascular system, and/or the like of the patient.

As described herein, the dosing mechanism may be supplied with the medical substance via an external source (e.g., relative to the patient) or an internal source. For example, an external source may include a supply mechanism (e.g., a syringe, an electronic or hydraulic pump, and/or the like) that supplies the medical substance via a fluid line and/or intake of the orthopaedic implant. In such cases, the dosing mechanism may be configured to release the medical substance within a widely variable period of time and at precise or varying dosing regimens. The internal source may be a reservoir of the orthopaedic implant that permits the dosing mechanism to release the medical substance over an extended duration (e.g., relative to previous techniques). For example, the dosing mechanism may have a particular configuration (e.g., a physical configuration) that causes the medical substance in the reservoir to flow, over the extended duration, from the reservoir, through the dosing mechanism and into the surgical area. Accordingly, the orthopaedic implant may be configured with a dosing mechanism that is to administer a medical substance to a surgical area of the orthopaedic implant.

According to some implementations, the orthopaedic implant is designed and/or configured according to one or more data models to enable the orthopaedic implant to provide patient-specific performance characteristics. For example, the orthopaedic implant may be configured using a topology optimization model that enables the orthopaedic implant to provide optimal support (e.g., according to the topology optimization model) and enable administration of a medical substance at a desired and/or required dosage rate. For example, the topology optimization model may be configured to determine the configuration for the orthopaedic implant based on the type of orthopaedic implant (e.g., which bone the orthopaedic implant is to interface with), the dosage rate, whether the orthopaedic implant is to be resupplied with the medical substance, and/or the like.

In this way, an orthopaedic implant, as described herein, is configured to permit direct administration and/or an accurate dosage (e.g., relative to previous techniques) of a medical substance to a surgical area of the orthopaedic implant by being configured to accurately release a dosage of the medical substance to the surgical area (relative to previous techniques). For example, the orthopaedic implant may be configured to release an antibiotic (and/or other type of antimicrobial agent, such as an antifungal agent, a DNase, and/or the like) to the surgical area to prevent the orthopaedic implant from causing an infection in the surgical area or to treat an infection in the surgical area. Such an orthopaedic implant (with a potentially percutaneously refillable chamber) reduces the likelihood that the patient would require additional surgeries (e.g., a revision surgery and/or a surgery to place a PICC line, an antibiotic spacer, and/or the like) following a surgical procedure to place the orthopaedic implant. Such surgeries may not be needed because the orthopaedic implant can ensure that adequate volumes and/or concentrations of the antibiotic and any adjuvant agents are being delivered locally (rather than systemically) and over an adequate duration of time (e.g., a duration longer than 4 weeks, 6 weeks, and/or the like). Furthermore, the ability to infuse antibiotics in this case may eliminate the necessity to use thermo-stable antibiotic agents (e.g., aminoglycosides or vancomycin) that are required with antibiotic cement due to the need to prevent denaturation during an exothermic polymerization reaction of a polymethylmethacrylate.

Moreover, an orthopaedic implant configured to prevent an infection through release of an antibiotic can be used at the time of a first total joint surgery (e.g., a primary orthopaedic surgery) to continue to prevent infection from any source of contamination or bacterial seeding for several weeks after the surgery, thus preserving a sterile implant. Furthermore, if a patient is treated with an orthopaedic implant that is configured as described herein, the orthopaedic implant may be configured to be accessed percutaneously (e.g., in a radiology unit) without requiring surgery. In such cases, a supply mechanism can supply (or resupply) the orthopaedic implant with antibiotics to treat (and/or further treat) the infection without requiring an additional surgery (e.g., a multi-stage revision surgery). Alternatively, such an implant can be placed at the time of revision surgery if necessary, or in the setting of infection or bone loss, which presents an opportunity to use definitive hardware to directly treat the pathologic process. The orthopaedic implant may permit the patient to be similarly treated with pain medications to manage pain and/or supplements to facilitate and/or hasten healing (and/or bone growth) of the bone involved in the surgery to place the orthopaedic implant.

Although some example implementations are described herein with respect to orthopaedic implants for joint replacement, similar configurations of orthopaedic implants may be configured in other types of bone implants (e.g., intramedullary nails to treat infected non-unions or open fractures, or promote bone growth of fractures or areas of segmental bone loss), spine implants (e.g., interbody spine implants), or other orthopaedic implants.

FIG. 1 is a diagram of an example implementation 100 of an orthopaedic implant 110 described herein. The example orthopaedic implant 110 of FIG. 1 includes a structure 120, a dosing mechanism 130, and a reservoir 140. In example implementation 100, the orthopaedic implant of 110 may be a hip implant that is placed within a patient in association with or on bones of the patient. For example, as shown, orthopaedic implant 110 is implanted between a femur and a pelvis of the patient. As described herein, other types of orthopaedic implants (e.g., that interface with different bones) may include similar features to enable the administration of a medical substance to a patient as described herein.

Structure 120 may include one or more mechanical elements and/or configurations to permit the orthopaedic implant to articulate and/or provide support to the patient (e.g., in a similar manner as one or more bones that are replaced and/or supported by the orthopaedic implant). For example, structure 120 may be configured and/or designed according to the size, shape, density, stiffness, and/or the like of the bone of the patient with which the orthopaedic implant is to interact. More specifically, structure 120 may be defined based on one or more patient-specific characteristics (e.g., an age, weight, height, desired performance capability, required medical substances for treatment of the patient, and/or the like). In FIG. 1, structure 120 may interact with the pelvis and femur of the patient as in the case of hip arthroplasty. In other joint orthopaedic implant examples, an orthopaedic implant may integrate with other bones of the joint (e.g., a proximal tibia or distal femur for a knee arthroplasty, a proximal humerus or glenoid for a shoulder arthroplasty, and/or the like). Additionally, or alternatively, for an interbody spine implant, a structure of the orthopaedic implant may interface with one or more bones by providing support to the one or more bones and/or fitting between the one or more bones.

Dosing mechanism 130 is configured to release the medical substance to treat a particular health condition of the patient (e.g., following a surgery to assist with recovery from the surgery). Treatment of a health condition may include managing pain, healing an injury, preventing bone loss, preventing or treating a disease (e.g., an oncological condition, a pathological condition, a neoplastic skeletal condition, and/or the like), preventing or treating an infection, and/or the like). Accordingly, dosing mechanism 130 may be configured to release a medical substance that is to prevent or treat an infection (e.g., an antibiotic) in a surgical area (e.g., around the hip of the patient), provide healing (or bone growth) to the bone of the surgical area (e.g., a bone growth supplement), manage pain of the patient (e.g., via an opioid or non-opioid pain medication), treat a disease of the patient, and/or the like. Additionally, or alternatively, dosing mechanism 130 may be configured to release one or more other types of medical substances to treat one or more other diseases of the patient (e.g., an oncology agent (e.g., a chemotherapy agent) for a patient with cancer to salvage a limb of a patient and/or treat metastatic tumors), lubricants for a joint of the patient, and/or the like.

Dosing mechanism 130 may include one or more openings between the reservoir and the surgical area of the patient. For example, in FIG. 1, an opening in dosing mechanism 130 may include or correspond to one or more paths (e.g., holes and/or routes through dosing mechanism 130) to enable the medical substance to flow from reservoir 140 to the proximal femur, hip joint, and acetabulum of the patient, in the example of a hip arthroplasty. The femur, through natural processes, may absorb the medical substance and/or enable a body system (e.g., a cardiovascular system, a skeletal system, and/or the like) to redistribute the medical substance throughout the patient.

The configuration of the paths of dosing mechanism 130 may determine a dosage rate of the medical substance. For example, the quantity of paths, diameters of the paths, routes of the paths (e.g., including direction, changes in direction, and/or the like relative to the reservoir and the surgical area), the location of the paths, and/or the like may enable (e.g., passively) a volume and/or frequency at which the medical substance is released from dosing mechanism 130 into the surgical area of the patient. In some implementations, the configuration of the paths may be determined and/or based on one or more physical properties of the medical substance. For example, for a solid medical substance, a size, diameter, and/or shape of particulates of the medical substance may determine the size, shape, and/or routes of the paths. Additionally, or alternatively, for a fluid medical substance, a viscosity of the medical substance may determine the size, shape, and routes of paths of dosing mechanism 130.

According to some implementations, dosing mechanism 130 may be configured to release the medical substance based on a particular position of the patient. For example, an opening of dosing mechanism 130 may be positioned to release the medical substance from the reservoir based on gravity. More specifically, in the example of FIG. 1, an opening of dosing mechanism 130 may be located toward a distal end 150 of the orthopaedic implant so that the medical substance is released from the reservoir when the patient is standing. In such a case, the medical substance may be a pain medication that is configured to be released while the patient is standing due to the patient likely experiencing more pain while standing. On the other hand, the opening can be placed toward a proximal end 160 of the orthopaedic implant so that the medical substance is released when the patient is at rest (e.g., sitting, lying flat, and/or the like). According to some implementations, dosing mechanism 130 may be configured to release the medical substance based on a structural deformation (e.g., a bend, a flex, and/or the like of orthopaedic implant during certain activities) and/or a reservoir pressure change imposed by weight bearing (e.g., due to the reservoir being compacted (e.g., from standing, walking, running, and/or other activities). Additionally, or alternatively, a piezoelectric potential of a deformation of an implant (and/or bone) may be used to generate a potential in a device to trigger a release of the medical substance.

Accordingly, the physical configuration of dosing mechanism 130 may determine the dosage rate, location of the flow of the medical substance, and/or the timing of releasing the medical substance into the surgical area of the patient. Similarly, the paths of dosing mechanism 130 may be localized throughout the implant such that deformations (which may be relatively minute so that the structural integrity of orthopaedic implant 110 is maintained) of orthopaedic implant 110 force the contents of the paths (e.g., the medical substance) out by applying or imposing pressure within reservoir 140. In other words, orthopaedic implant 110 may be configured to correspondingly increase a reservoir pressure of reservoir 140 during certain patient activities (e.g., standing, walking, running, and/or the like) and/or due to certain structural deformations of orthopaedic implant 110.

Reservoir 140 may be any void (e.g., a space that is a vacuum and/or includes a gas, such as air or other type of gas) and/or chamber associated with structure 120. In some implementations, reservoir 140 may include a hydrogel, an internal lattice structure, a foam, and/or the like that governs release of the medical substance based on a pressure of reservoir 140 (e.g., a pre-loaded pressure, an applied pressure, and/or the like), electrical potential of the patient according to an electrical gradient between orthopaedic implant 110 and tissue of the patient, efflux channel properties of dosing mechanism 130, and/or the like. For example, reservoir 140 may be within a frame (or perimeter) of structure 120, a component of structure 120, coupled with structure 120, and/or the like. According to some implementations, the dimensions of reservoir 140 may be configured and/or determined based on one or more structural requirements (e.g., strength, stiffness, and/or the like) of the orthopaedic implant. In some implementations, reservoir 140 is configured according to a topology optimization for the orthopaedic implant (e.g., according to patient-specific bone structure). Additionally, or alternatively, structure 120 and/or dosing mechanism 130 may be configured according to the topology optimization model. Accordingly, orthopaedic implant 110 may be configured to optimize a performance characteristic for a patient. Such a performance characteristic may correspond to the ability to administer the medical substance and/or one or more other performance characteristics (e.g., an ability to withstand a threshold force, limit stress shielding, have a particular porosity, resist fatigue, and/or the like).

In some implementations, a capacity and/or a volume of reservoir 140 may be based on a concentration of a dosage of the medical substance that is to be provided from reservoir 140 and/or an amount of the medical substance that is to be stored in reservoir 140 (which may correspond to a length of a time period over which the medical substance is to be stored and/or released from reservoir 140, and correspondingly, administered to the patient).

In some implementations, orthopaedic implant 110 may include an intake mechanism through which reservoir 140 is to be supplied with medical substance. The intake mechanism may enable the medical substance to be supplied from a source (e.g., a supply mechanism, such as a pump) and/or by an individual (e.g., a doctor or other medical professional).

In this way, orthopaedic implant 110 is configured to administer a medical substance to a surgical area of the patient while interfacing with one or more bones of the patient (e.g., to treat an orthopaedic condition of the patient).

As indicated above, FIG. 1 is provided merely as one or more examples. Other examples may differ from what is described with regard to FIG. 1.

Figure 2:
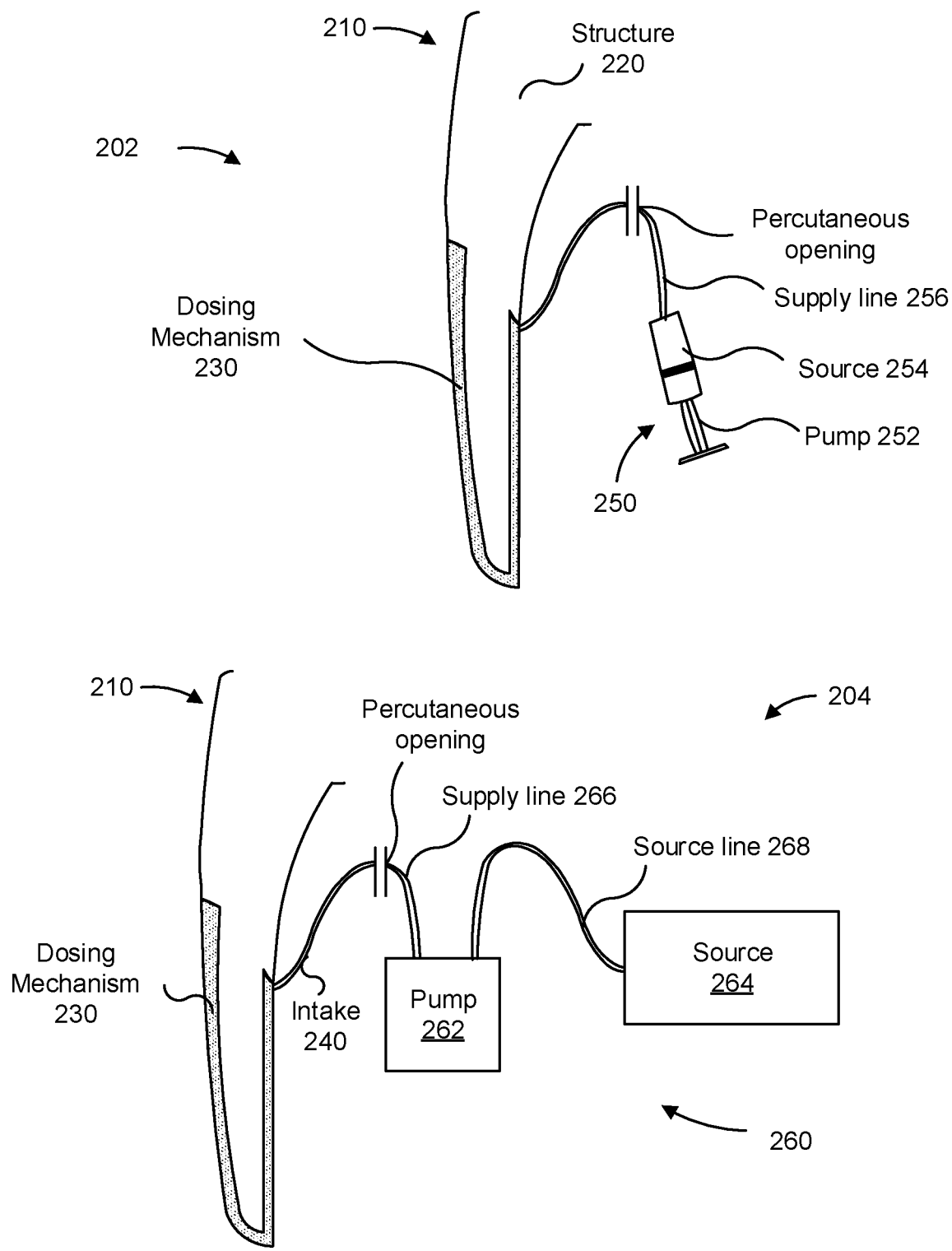
FIG. 2 is a diagram of one or more example implementations of a system associated with an orthopaedic implant described herein.

FIG. 2 is a diagram of example implementations of a system associated with an orthopaedic implant described herein. FIG. 2 includes a first system 202 and a second system 204 (referred to herein as the "systems") that include an orthopaedic implant 210. Orthopaedic implant 210 includes a structure 220 (which may correspond to structure 120), a dosing mechanism 230 (which may correspond to dosing mechanism 130), and an intake 240. Intake 240 may include any suitable structure (e.g., a line, such as a tube, that enables the flow of a medical substance into dosing mechanism 230). In some implementations, orthopaedic implant 210 may include a reservoir (e.g., similar to reservoir 140) (e.g., positioned between intake 240 and dosing mechanism 230 to temporarily hold or store a medical substance, as described herein).

The first system 202 includes a first supply mechanism 250. The first supply mechanism 250 may include a pump 252 (e.g., a manual pump, such as a syringe), a source 254, and a supply line 256. Pump 252 is configured to supply a medical substance from source 254 to dosing mechanism 230. The first supply mechanism 250 may supply the dosing mechanism 230 with the medical substance via supply line 256. Supply line 256 may be coupled with intake 240 via a percutaneous opening of the patient. Additionally, or alternatively, a coupling mechanism, such as a line connector, a fitting, a fastener, a locking mechanism, a port, and/or the like, may be used to couple supply line 256 with intake 240.

The second system 204 includes a second supply mechanism 260. The second supply mechanism 260 may include a pump 262 (e.g., an electronic pump, a hydraulic pump, and/or the like), a source 264, a supply line 266, and a source line 268. Pump 262 is configured to supply the medical substance from source 264 to dosing mechanism 230. The second supply mechanism 260 may supply the dosing mechanism 230 with the medical substance via supply line 266 and source line 268. Supply line 266 may be coupled (e.g., via a coupling mechanism) with intake 240 via a percutaneous opening of the patient.

Accordingly, the systems of FIG. 2 may enable dosing mechanism 230 to be directly supplied with a medical substance to permit dosing mechanism 230 to release the medical substance into a surgical area of orthopaedic implant 210. Dosing mechanism 230 may be configured with one or more paths to permit the perfusion of the medical substance through dosing mechanism 230 and omnidirectionally from dosing mechanism 230. For example, dosing mechanism 230 may include a porous structure configured to retain the medical substance until dosing mechanism 230 is saturated with the medical substance. In such cases, once dosing mechanism 230 is saturated (e.g., according to a capacity of dosing mechanism 230), dosing mechanism 230 may be configured to enable the medical substance to be released from dosing mechanism 230. Without a reservoir (similar to reservoir 140), dosing mechanism 230 may be configured to allow the medical substance to be administered within a shorter period of time, relative to dosing mechanism 230 releasing the medical substance from a reservoir of orthopaedic implant 210. Dosing mechanism 230 may be configured to release the medical substance according to a rate at which the supply mechanisms 250, 260 supply dosing mechanism 230. For example, the faster the supply mechanisms 250, 260 supply dosing mechanism 230 with the medical substance, the faster dosing mechanism is to release the medical substance and/or the slower the supply mechanisms 250, 260 supply dosing mechanism 230 with the medical substance, the slower dosing mechanism 230 is to release the medical substance.

In some implementations, intake 240 may include multiple lines to permit the flow of the medical substance into a reservoir and dosing mechanism 230. Accordingly, an individual (e.g., a doctor or surgeon) may supply the reservoir with the medical substance (e.g., for long-term release of the medical substance) and/or dosing mechanism 230 with the medical substance (e.g., for short-term release and/or long-term release) depending on the medical substance that is being supplied and/or an effective duration during which the medical substance is to be administered.

As indicated above, FIG. 2 is provided merely as one or more examples. Other examples may differ from what is described with regard to FIG. 2. Furthermore, the first system 202 and the second system 204 may be used simultaneously, one after the other, one instead of the other (e.g., based on preferences or conditions of the patient), and/or the like.

Figure 3:
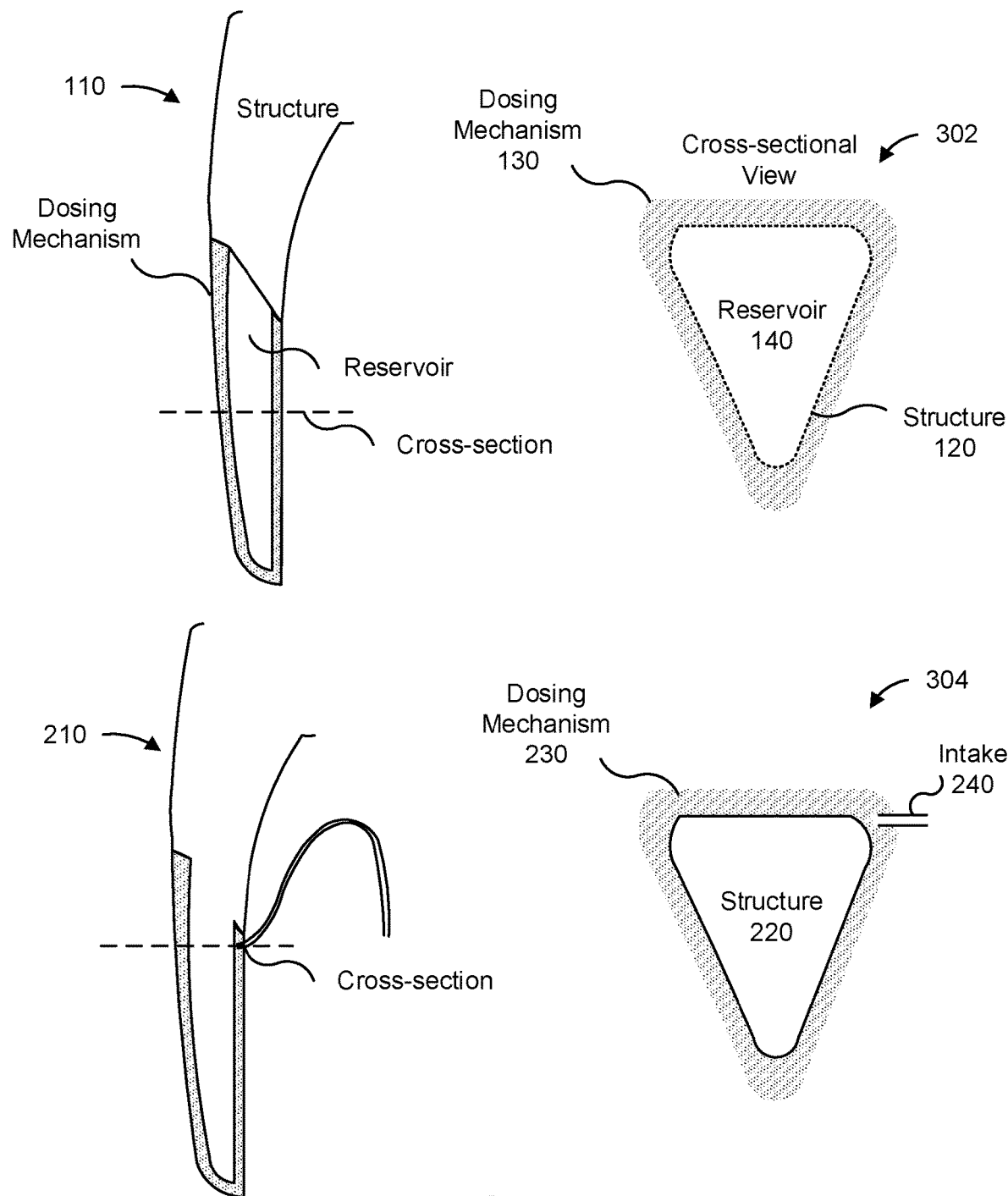
FIG. 3 is a diagram of cross-sectional views of example implementations of an orthopaedic implant described herein.

FIG. 3 is a diagram of cross-sectional views of example implementations of an orthopaedic implant described herein. In a cross-sectional view 302 of orthopaedic implant 110 (e.g., corresponding to orthopaedic implant 110 of FIG. 1), reservoir 140 is shown within structure 120. Structure 120 includes a plurality of openings (as shown by the dotted line) which may correspond to and/or be a part of dosing mechanism 130.

In cross-sectional view 304 of orthopaedic implant 210 (e.g., corresponding to orthopaedic implant 210 of FIG. 2), structure 220 is shown without any openings (as shown by the solid line). Structure 220 may be solid and/or hollow (e.g., depending on the design of orthopaedic implant 210 as configured by a topology optimization). Intake 240 may be configured to enable the flow of medical substance into dosing mechanism 230, which may be configured to distribute and/or release the medical substance (e.g., once saturated with the medical substance).

As indicated above, FIG. 3 is provided merely as one or more examples. Other examples may differ from what is described with regard to FIG. 3.

Figure 4A:
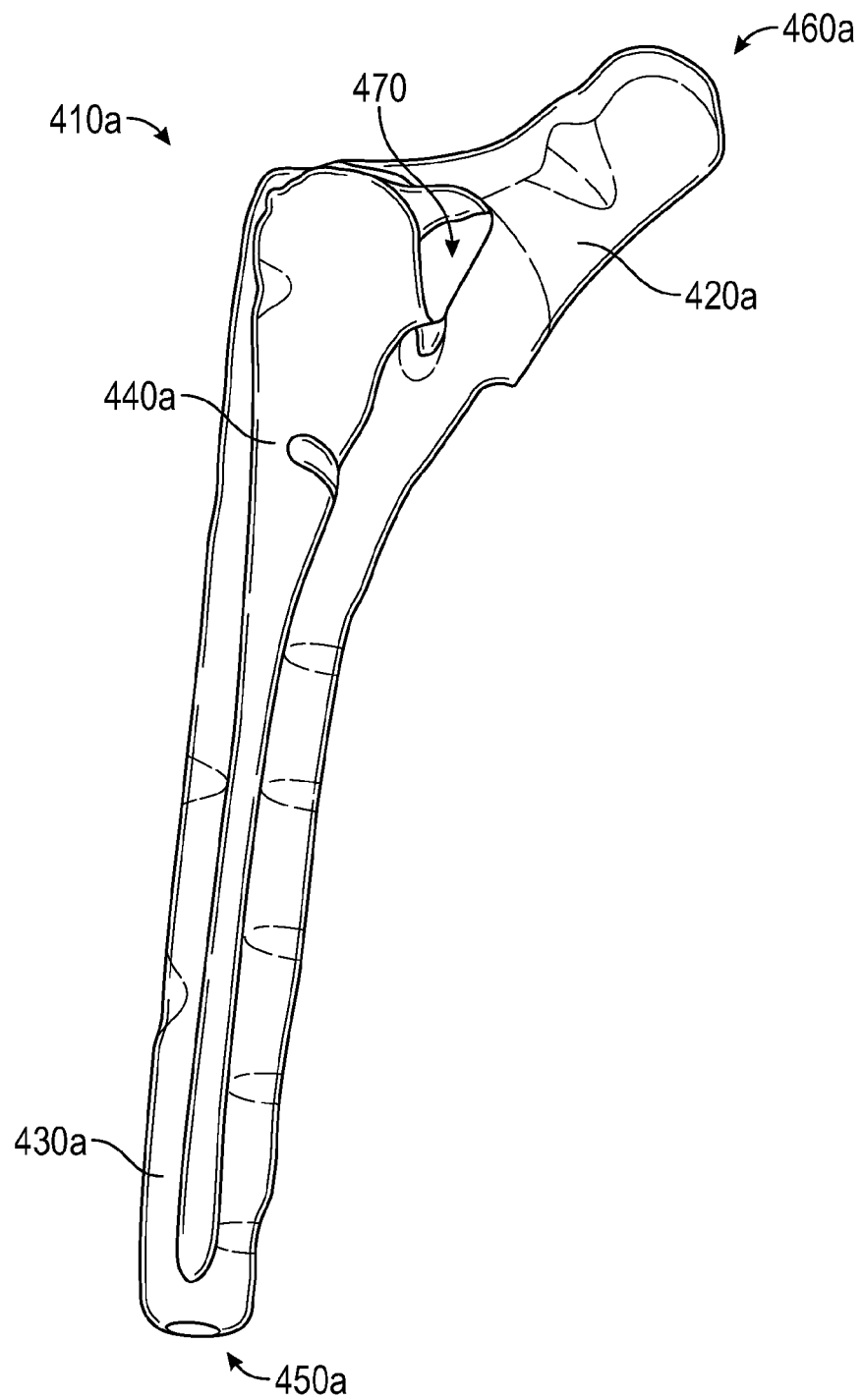
FIGS. 4A-4C are illustrations of example implementations of orthopaedic implants described herein.
Figure 4B:
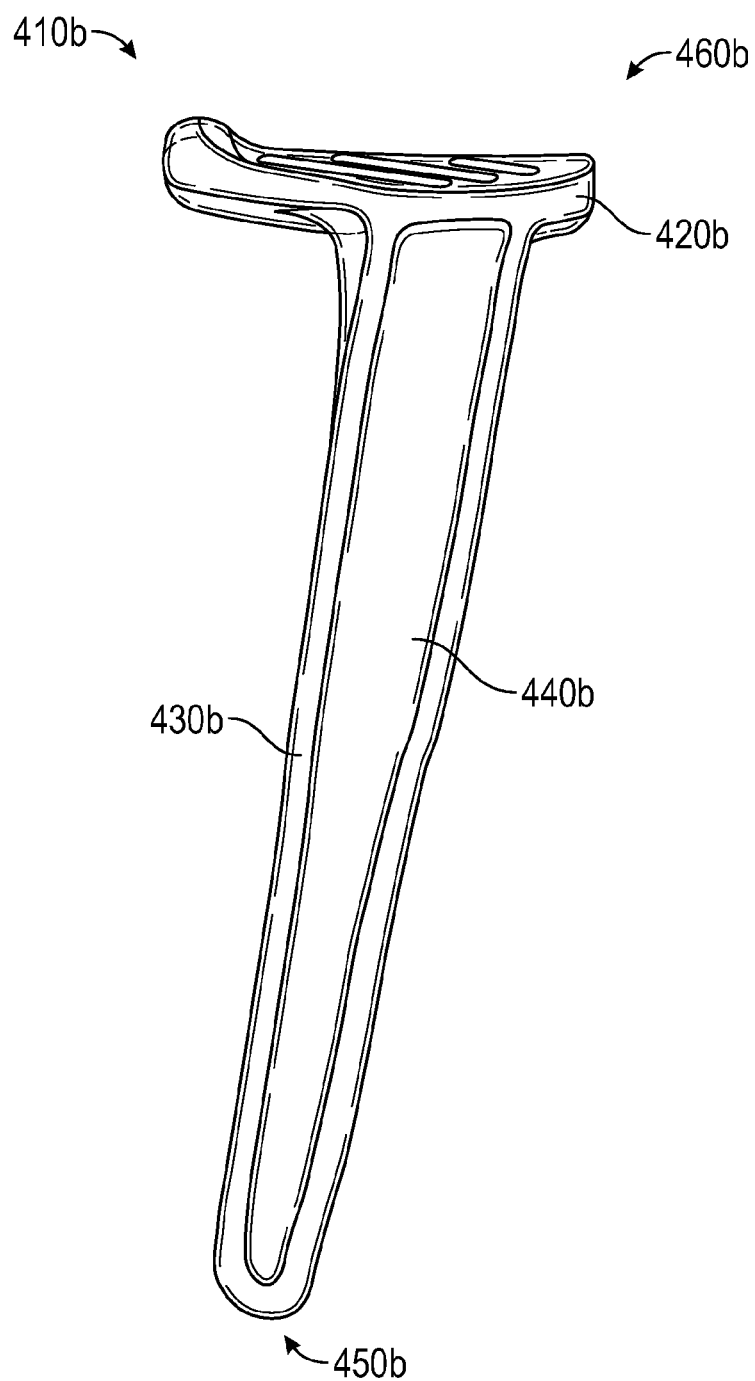
Figure 4C:
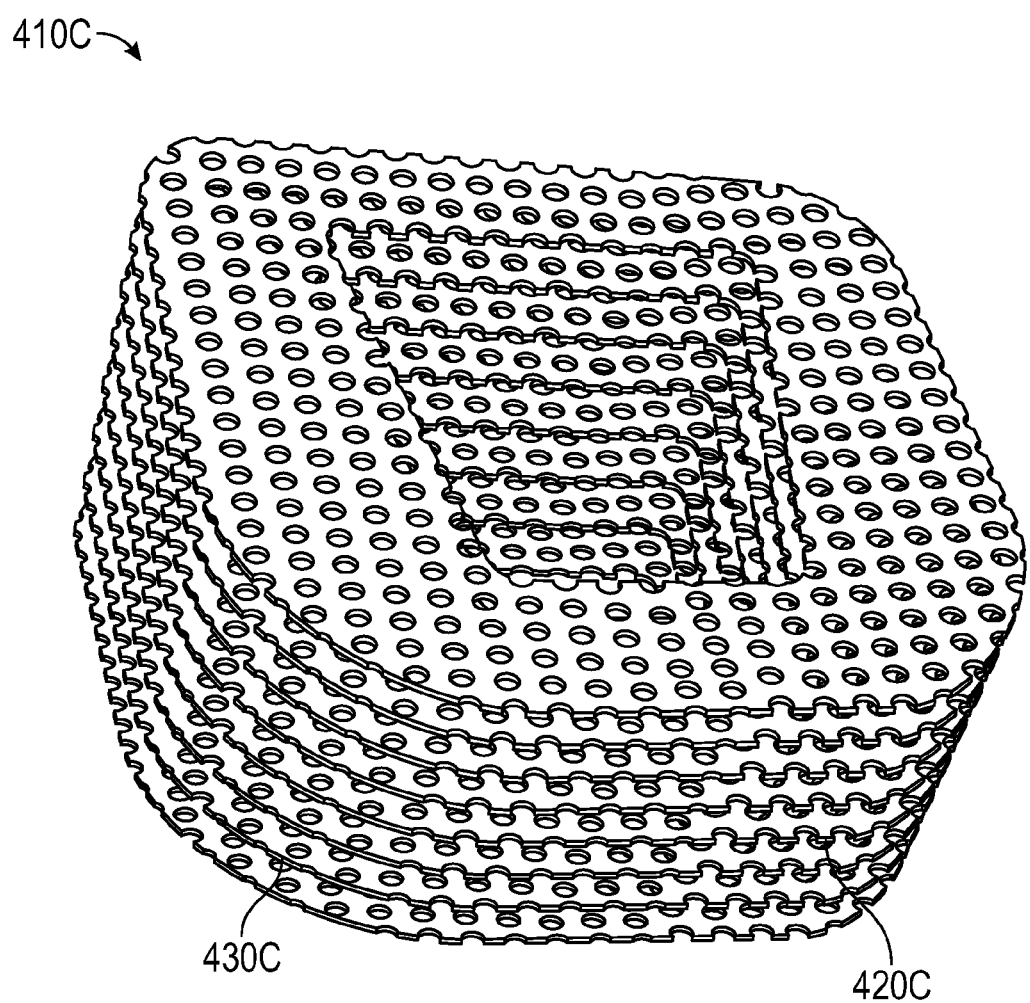

FIGS. 4A-4C are illustrations of example implementations of orthopaedic implants described herein. FIG. 4A includes an isometric view of an example hip implant 410a configured in accordance with examples described herein. Hip implant 410a includes a structure 420a, a dosing mechanism 430a, and a reservoir 440a (which may correspond to structure 120, dosing mechanism 130, and reservoir 140 of FIG. 1, respectively). Dosing mechanism 430a of hip implant 410a is configured to release the medical substance from reservoir 440a. In some implementations, dosing mechanism 430a may include an opening in structure 420a that is positioned toward a distal end 450a of hip implant 410a (e.g., to permit gravitational release of the medical substance). As further shown in FIG. 4A, hip implant 410a includes a void 470 toward proximal end 460a. Void 470 may be designed and/or formed within hip implant 410a according to a topology optimization model, as described herein.

FIG. 4B includes an isometric view of an example knee implant 410b configured in accordance with examples described herein. Knee implant 410b includes a structure 420b, a dosing mechanism 430b, and a reservoir 440b (which may correspond to structure 120, dosing mechanism 130, and reservoir 140 of FIG. 1, respectively). Dosing mechanism 430b of knee implant 410b may include one or more openings in structure 420b to enable medical substance to flow from reservoir 440b into a surgical area between distal end 450b and proximal end 460b.

FIG. 4C includes an isometric view of an example interbody spine implant 410c configured in accordance with examples described herein. Interbody spine implant 410c may be configured to fit between spine segments of a patient. Interbody spine implant 410c includes a lattice structure 420c (e.g., which may be similar to trabecular bone of a patient). A dosing mechanism 430c may be included within and/or as part of lattice structure 420c to enable the perfusion of a medical substance through lattice structure 420c and/or between segments of a spine of the patient, in accordance with examples described herein.

As indicated above, FIGS. 4A-4C are provided merely as one or more examples. Other examples may differ from what is described with regard to FIGS. 4A-4C.

Figure 5:
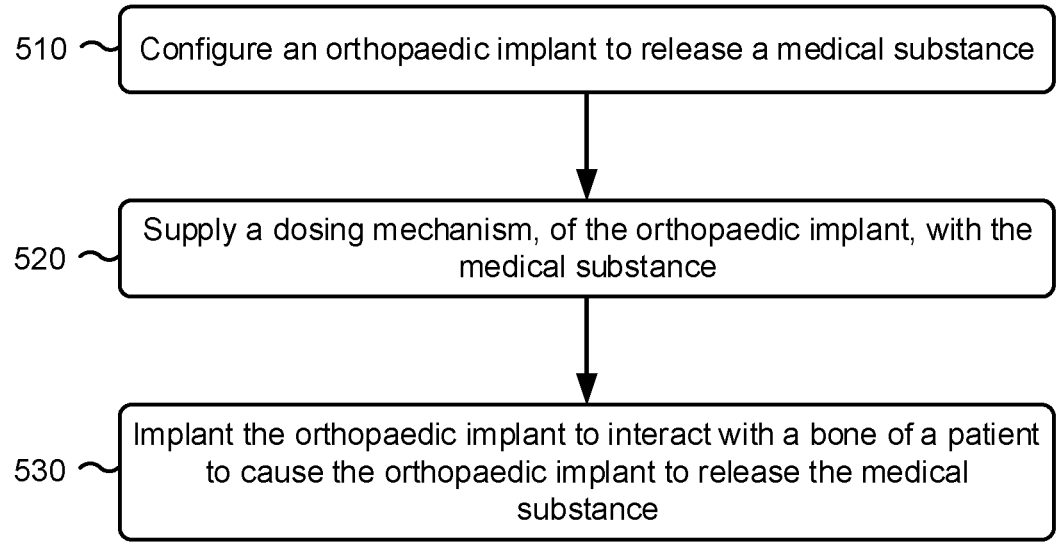
FIG. 5 is a flowchart of an example process associated with an orthopaedic implant to administer a medical substance.

FIG. 5 is a flowchart of an example process associated with an orthopaedic implant to administer a medical substance, as described herein. In some implementations, one or more process blocks of FIG. 5 may be performed using an orthopaedic implant system (e.g., the orthopaedic implant system). Such an orthopaedic implant system may include a user device, a medical imaging device, a manufacturing device, and/or a platform (e.g., an implant customization platform) for configuring an orthopaedic implant to administer a medical substance, as described herein.

As shown in FIG. 5, process 500 may include configuring an orthopaedic implant to release a medical substance (block 510). The orthopaedic implant may be configured according to one or more data models as described in U.S. patent application Ser. No. 17/597,221, titled "CUSTOMIZATION OF AN ORTHOPAEDIC IMPLANT" and filed on Jul. 22, 2020, which is hereby incorporated by reference. For example, the orthopaedic implant may be configured using an image processing model, a topology optimization model, and/or the like to enable patient-specific administration and/or dosing of the medical substance and provide a configuration that optimally matches a bone structure of the patient (e.g., according to the one or more data models).

As further shown in FIG. 5, process 500 may include supplying a dosing mechanism, of the orthopaedic implant, with the medical substance (block 520). For example, the dosing mechanism may be configured to receive the medical substance to release the medical substance at a particular dosage rate (e.g., that is enabled according to a configuration of the dosing mechanism).

In some implementations, the dosing mechanism is supplied with the medical substance via a reservoir within a structure of the orthopaedic implant. As described herein, the reservoir may hold the medical substance for a particular period of time (e.g., corresponding to an effective duration for the medical substance). The reservoir may be supplied with the medical substance prior to and/or during a surgical procedure to implant the orthopaedic implant. Additionally, or alternatively, the reservoir may be supplied (e.g., resupplied or refilled) with the medical substance after the surgical procedure to implant the orthopaedic implant. For example, the reservoir may be supplied via a supply mechanism that is external to the patient following the procedure. In such cases, the supply mechanism may be coupled with the reservoir (e.g., via an intake mechanism of the orthopaedic implant) percutaneously to enable the medical substance to flow from an external source to the reservoir.

Additionally, or alternatively, the dosing mechanism may be directly supplied with the medical substance via the supply mechanism (e.g., if the orthopaedic implant is configured without a reservoir, if the medical substance is to be administered immediately and/or within a relative short time (e.g., within a minute, within 5 minutes, and/or the like) of being supplied with the medical substance.

As further shown in FIG. 5, process 500 may include implanting the orthopaedic implant to interact with a bone of a patient to cause the orthopaedic implant to release the medical substance (block 530). For example, the orthopaedic implant may be implanted within the patient via one or more orthopaedic procedures according to the configuration of the orthopaedic implant. Such orthopaedic surgical procedures may include one or more of creating one or more incisions in tissue of the patient, removing and/or shaping one or more bones of the patient, fixing the orthopaedic implant to the one or more bones and/or between the one or more bones, configuring an intake to the orthopaedic implant through the tissue (e.g., if the orthopaedic implant is to be supplied with medical substance after the surgical procedure), and/or closing the one or more incisions.

Although FIG. 5 shows example blocks of process 500, in some implementations, process 500 may include additional blocks, fewer blocks, different blocks, or differently arranged blocks than those depicted in FIG. 5. Additionally, or alternatively, two or more of the blocks of process 500 may be performed in parallel.

The foregoing disclosure provides illustration and description but is not intended to be exhaustive or to limit the implementations to the precise forms disclosed. Modifications and variations may be made in light of the above disclosure or may be acquired from practice of the implementations.

As used herein, the term "component" is intended to be broadly construed as hardware, firmware, and/or a combination of hardware and software.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, a combination of related and unrelated items, etc.), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. An orthopaedic implant for treating a patient comprising:
   a structure configured to interact with a bone of the patient,
      wherein the structure is configured based on patient-specific characteristics;
   a reservoir associated with the structure to hold a medical substance for treating a health condition of the patient; and
   a dosing mechanism to release the medical substance to treat the health condition,
      wherein the dosing mechanism comprises a set of paths configured to enable the medical substance to flow from the reservoir at a dosage rate,
      wherein a route of the set of paths is determined based on one or more physical properties of the medical substance, and
      wherein the dosing mechanism is configured to release the medical substance from the dosing mechanism within a variable period of time and to vary a frequency at which the medical substance is released in accordance with the dosage rate.

2. The orthopaedic implant of claim 1, wherein treating the health condition is associated with at least one of:
   preventing or treating an infection,
   healing the bone of the patient,
   managing pain of the patient,
   treating an oncological condition,
   treating a pathologic condition, or
   treating a neoplastic musculoskeletal conditions.

3. The orthopaedic implant of claim 1, further comprising an intake mechanism that supplies the reservoir with the medical substance, and wherein a size, shape, and the route of the set of paths are determined based on one or more physical properties of the medical substance.

4. The orthopaedic implant of claim 3, wherein the intake mechanism is configured to be accessible after the orthopaedic implant is implanted within the patient, and wherein the medical substance comprises a plurality of particulates and the one or more physical properties of the medical substance includes one or more of a size, a diameter, or a shape of the plurality of particulates.

5. The orthopaedic implant of claim 3, wherein the intake mechanism includes a coupling mechanism that is capable of coupling with a supply mechanism that supplies the medical substance.

6. The orthopaedic implant of claim 1, wherein the medical substance comprises a fluid and the route of the set of paths is configured to enable the fluid to flow between the reservoir and a surgical area of the orthopaedic implant at the dosage rate based on a viscosity of the fluid.

7. The orthopaedic implant of claim 6, wherein a size, a shape, and the route of the set of paths are determined based on the viscosity of the fluid to cause the medical substance to be released at the dosage rate.

8. The orthopaedic implant of claim 6, wherein one or more openings corresponding to one or more ends of the set of paths are positioned within the structure to permit the medical substance to be released based on at least one of:
   a structural deformation, or
   a reservoir pressure change.

9. The orthopaedic implant of claim 1, wherein at least one of the structure, the reservoir, or the dosing mechanism are configured according to a topology optimization model,
   wherein the topology optimization model is configured to design the orthopaedic implant based on the patient-specific characteristics.

10. The orthopaedic implant of claim 1, wherein the orthopaedic implant comprises at least one of:
a bone implant, or
an interbody spine implant.

11. A medical substance dosing system comprising:
an orthopaedic implant comprising:
a structure configured to interact with a bone of a patient according to one or more patient-specific characteristics, and
a dosing mechanism to release a medical substance to treat a health condition of the patient,
wherein the dosing mechanism comprises a set of paths configured to enable the medical substance to flow from the structure at a dosage rate,
wherein a route of the set of paths through the structure is determined based on one or more physical properties of the medical substance, and
wherein the dosing mechanism is configured to release the medical substance from the dosing mechanism within a variable period of time and to vary a frequency at which the medical substance is released in accordance with the dosage rate; and
a supply mechanism configured to supply the dosing mechanism with the medical substance.

12. The medical substance dosing system of claim 11, wherein the supply mechanism comprises:
a source of the medical substance; and
a pump.

13. The medical substance dosing system of claim 11, wherein the orthopaedic implant is implanted within the patient.

14. The medical substance dosing system of claim 11, wherein the dosing mechanism comprises an opening situated between the structure and a surgical area of the orthopaedic implant, wherein the opening corresponds to an end of a path of the set of paths of the dosing mechanism.

15. The medical substance dosing system of claim 14, wherein a size and shape of the opening has a configuration to release the medical substance at the dosage rate.

16. The medical substance dosing system of claim 14, wherein the opening is positioned within the structure to permit the medical substance to be released based on at least one of:
a structural deformation caused by weight bearing, or
a reservoir pressure change imposed by weight bearing.

17. The medical substance dosing system of claim 11, wherein the orthopaedic implant comprises at least one of:
a bone implant, or
an interbody spine implant.

18. A method for providing a medical substance to treat a patient, wherein the method comprises:
configuring an orthopaedic implant to release the medical substance according to one or more patient-specific characteristics of the patient;
supplying a dosing mechanism, of the orthopaedic implant, with the medical substance,
wherein the dosing mechanism comprises a set of paths configured to enable the medical substance to be released at a dosage rate,
wherein a route of the set of paths is determined based on one or more physical properties of the medical substance, and
wherein the dosing mechanism is configured to release the medical substance from the dosing mechanism within a variable period of time and to vary a frequency at which the medical substance is released in accordance with the dosage rate; and
implanting the orthopaedic implant to interact with a bone of a patient to cause the orthopaedic implant to release the medical substance in accordance with the dosage rate.

19. The method of claim 18, wherein the dosing mechanism is supplied with the medical substance via a reservoir within a structure of the orthopaedic implant,
wherein the reservoir holds the medical substance for a particular period of time.

20. The method of claim 18, wherein the dosing mechanism is supplied with the medical substance via a supply mechanism that is external to the patient.

* * * * *